US005804195A

United States Patent [19]
Gutter

[11] Patent Number: 5,804,195
[45] Date of Patent: Sep. 8, 1998

[54] VACCINE COMPRISING AN INFECTIOUS BURSAL DISEASE VIRUS MB, MB-1 OR MB-2 STRAIN

[75] Inventor: Bezalel Gutter, Jerusalem, Israel

[73] Assignee: ABIC Ltd., Netanya, Israel

[21] Appl. No.: 159,424

[22] Filed: Nov. 30, 1993

[30] Foreign Application Priority Data

Dec. 1, 1992 [IL] Israel .......... 103939

[51] Int. Cl.$^6$ .......... A61K 39/12; A61K 39/295; C12N 7/00; C12N 7/02; C12N 7/11; C12N 7/12
[52] U.S. Cl. .......... 424/202.1; 424/204.1; 424/816; 435/235.1; 435/236; 435/237; 435/239
[58] Field of Search .......... 424/89, 204.17, 424/204.1, 816, 202.1; 435/235.1, 236, 237, 239

[56] References Cited

U.S. PATENT DOCUMENTS

| 4,530,831 | 7/1985 | Lutticken et al. | 424/202.1 |
|---|---|---|---|
| 4,824,668 | 4/1989 | Melchoir et al. | 424/202.1 |
| 5,064,646 | 11/1991 | Synder | 424/147.1 |

FOREIGN PATENT DOCUMENTS 9105569  5/1991  WIPO.

OTHER PUBLICATIONS

Snyder et al. Avian Pathology 19:419–423 1990.
Kibenge et al., "Biochemistry and Immunology of Infectious Bursal Disease Virus", *J. Gen. Virol.* (Great Britain) 69:1757–1775 (1988).

*Primary Examiner*—Anthony C. Caputa
*Attorney, Agent, or Firm*—Kohn & Associates

[57] ABSTRACT

Invention relates to a vaccine for the prevention of Infectious Bursal Disease in poultry comprising an effective immunizing amount of a live attenuated intermediately-pathogenic IBD virus belonging to the strain deposited at the ECACC under No. V92052301 (MB), an effective immunizing amount of a live attenuated intermediately-pathogenic IBD virus belonging to the strain deposited at the ECACC under No. V92100106 (MB-2), or an effective immunizing amount of a live attenuated intermediately-pathogenic IBD virus belonging to the strain deposited at the ECACC under No. V92102209 (MB-1).

19 Claims, 1 Drawing Sheet

VACCINE COMPRISING AN INFECTIOUS BURSAL DISEASE VIRUS MB, MB-1 OR MB-2 STRAIN

FIELD OF THE INVENTION

The invention concerns novel Infectious Bursal Disease (IBD) vaccines and novel Infectious Bursal Disease attenuated viral strains.

BACKGROUND OF THE INVENTION

Infectious Bursal Disease in poultry is caused by a virus which belongs to the BIRNA group of viruses. These viruses are relatively stable at low pH, ether and chloroform. They contain two fragments of double-stranded RNA which encode their viral proteins.

Two serotypes are known, namely Serotype I, which causes the IBD in chickens and serotype II, isolated from turkeys, not pathogenic to chickens. Maternal antibodies to one serotype do not protect against the other serotype. Homologous antibodies do, however, protect chicks against the disease.

Infectious Bursal Disease is widespread and causes great economic losses. Afflicted chickens suffer from diarrhea, muscular hemorrhage, necrosis of the bursa of Fabricius and severe damage to the immune system. The mortality is high and the surviving chickens exhibit growth retardation and high sensitivity to other diseases.

Several live attenuated vaccines were developed over the years. For example, U.S. Pat. No. 3,584,055 discloses a vaccine effective against IBD containing attenuated IBD virus obtained through multiple passages. U.S. Pat. No. 3,769,400 discloses a vaccine effective against IBD containing attenuated IBD virus obtained through passages in baby mice. U.S. Pat. No. 4,530,831 discloses a live or inactivated vaccine effective against IBD in poultry on a single administration to the birds at the usual age of vaccination, which comprises IBD virus deposited as ATCC VR-2041. The vaccine is non-pathogenic and can break through the usual level of maternally derived antibodies without damage to the bursa of the maternally immune birds, and is therefore used to confer protection to poultry. The vaccine is obtained by a 4-step plaque purification, followed by two egg passages. U.S. Pat. No. 4,824,668 discloses a vaccine effective against IBD in poultry comprising an attenuated or inactivated IBD virus strain VR2161 and a carrier or diluent, which can be administered to poultry without producing IBD symptoms in the vaccinated birds. Such vaccines were usually administered via drinking water, and, until 1988, they conferred good immunity. PCT Application WO 9001336 discloses a vaccine for preventing IBD in poultry caused by strains not responsive to vaccines known at the time (apparently "non-classic" strains), containing a killed or attenuated novel purified IBD virus as described therein.

In 1988, first in England and Holland and afterwards in other parts of the world, a new strain appeared which was very pathogenic and caused much higher mortality rates than those caused by the "old" strains. The existing live attenuated vaccines no longer protected against the new strain. The new strain isolated in Europe was not found to be antigenically different from the old, so-called "classic" strain. On the other hand, in the U.S. "variant" strains were isolated that differ from the "classic" strains when tested with monoclonal antibodies test systems. The Israeli isolates which are the subject of this invention were tested and found to be similar to the European strains.

The inefficiency of the old vaccines to protect against the new strains is caused, inter alia, by the higher pathogenicity of the new strains capable of penetrating through the maternal antibodies transferred from breeder hens to chicks. Upon vaccination of the newly hatched chicks the viruses of the old thus introduced are inactivated by such maternal antibodies. The maternal antibody titer decreases after hatching with a half-life of about 5 days. If vaccination is postponed to an age at which no maternal antibodies can be detected, the chickens are at a very high risk: they may be infected by a pathogenic field strain before being immunized by the vaccine strain. It is therefore believed that a vaccine strain should have some pathogenicity, so that it would break through maternal antibodies before field strains do, namely it should be of an intermediate virulence.

Recently, H. J. Tsai and Y. M. Saif [Avian Diseases 36:415–422 (1992)] described two variant strains of IBD (IN and E), which were adapted and passaged in an established green monkey kidney cell line (BGM-70). Passage in cell culture resulted in loss of pathogenicity, while antigenicity and immunogenicity were maintained. However, no protection against the disease was induced when the passaged viruses were given to specific-pathogen-free (SPF) chickens as live vaccines. In contrast, the present invention relates to viruses which were passaged, lost some of their pathogenicity, but retained antigenicity and do confer immunity to poultry.

SUMMARY OF THE INVENTION

The invention relates to a vaccine for the prevention of Infectious Bursal Disease in poultry comprising an effective immunizing amount of a live attenuated intermediately-pathogenic IBD virus belonging to the strain deposited at the ECACC under No. V92052301 (MB).

The invention also relates to a vaccine for the prevention of Infectious Bursal Disease in poultry comprising an effective immunizing amount of a live attenuated intermediately-pathogenic IBD virus belonging to the strain deposited at the ECACC under No. V92100106 (MB-2).

The invention further relates to a vaccine for the prevention of Infectious bursal disease in poultry comprising an effective immunizing amount of a live attenuated intermediately-pathogenic IBD virus belonging to the strain deposited at the ECACC under No. V92102209 (MB-1).

In addition, the invention relates to a method of preventing Infectious Bursal disease in poultry by administering to the birds an effective immunizing amount of a vaccine containing the IBD virus of the strains deposited at the ECACC under No. V92052301 (MB) and/or No. 92100106 (MB-2) and/or No. V92102209 (MB-1).

In a further aspect, the invention relates to three novel virus strains deposited at the ECACC under No. V92052301 (MB), under No. V92100106 (MB-2) and under No. V92102209 (M-1).

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1A:
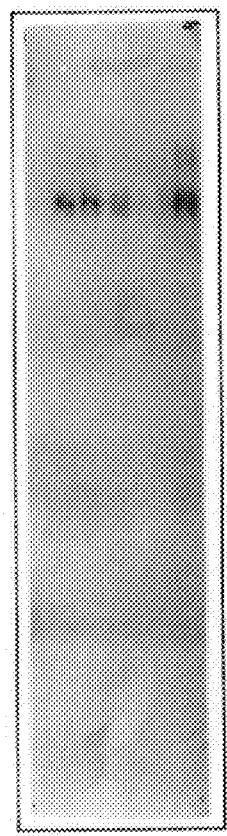
FIG. 1 is a picture of a western blot analysis.

Furthermore, the invention relates to a method of preparing live vaccines which protect poultry against Infectious Bursal Disease, containing an effective immunizing amount of a virus of the strain deposited at the ECACC under No. V92052301 (MB) and/or No. V92100106 (MB-2) and/or No. V92102209 (MB-1).

DETAILED DESCRIPTION OF THE INVENTION

The invention relates to three novel virus strains deposited at the ECACC under No. V92052301 (MB), under No. V92100106 (MB-2) and under No. V92102209 (MB-1). The deposit was at the ECACC (European Collection of Animal Cell Cultures), PHLS Centre for Applied Microbiology & Research, Porton Down, Salisbury, Wilts, SP4 OJG, U.K.

As stated above, vaccination of poultry should be effected at an early age, before disappearance of maternal antibodies, to avoid exposure of chicks to the high risk of being infected by pathhogenic field strains. Therefore it is believed that a potent vaccine strain should maintain some pathogenicity, so that it would break through maternal antibodies. The three novel strains of the invention, MB, MB-2 and MB-1, pose this desired characteristic, being intermediately pathogenic, thus breaking through maternal immunity, but not so virulent as to cause disease. When tested in SPF chicks free of IBD antibodies, strain MB-1 was somewhat less pathogenic than strain MB, and strain MB-2 even less pathogenic. All three strains confer good immunity when administered, via drinking water, even at the early age of 1–2 weeks and are non-pathogenic for maternally immune broiler chicks or replacement breeder and layer chicks. A certain degree of bursal atrophy does however occur following vaccination.

The original strains were isolated from bursae of Fabricius of broiler chickens that died of IBD on two farms in the central part of Israel during the year of 1989. The virus can be grown in embryonated chicken eggs, as well as in cell cultures such as chicken embryo fibroblast (CEF) tissue culture, vero cell line cultures and other suitable cultures. Cells are grown to 80% confluency on roller bottles, flasks, microcarriers or other methods serving for growing tissue cultures. 3–4 days following infection, cytopathic effect (CPE) is formed and the virus is harvested by freezing and thawing, followed by low speed centrifugation. Stabilizers are added to the supernatant for freeze drying process. Attenuation and propagation of the virus will be described in detail in the following Examples.

Preparation of vaccines and their administration is also within the scope of the invention. Embryonated eggs were inoculated, the embryos and membranes harvested and a live vaccine prepared from a homogenate prepared from them with the addition of a stabilizer normally used in live avian vaccines such as peptone, lactose, dry powdered milk, etc.

A dosage may be used, as live vaccine, in the range of $10^2$–$10^4$ $EID_{50}$ ($EID_{50}$=egg infective dose 50%).

A live vaccine according to the invention can contain a single of said virus strains, or a mixture of any two of said strains, or further, a mixture of all said virus strains.

Any of the live vaccines of the invention may also contain other viruses, e.g., New Castle virus or Marek Disease virus or Infectious Bronchitis virus.

The vaccine is administered to chickens by presently available inoculation techniques, for example, via drinking water, through ocular administration as eye drops, aerosol or other spraying methods, through nasal administration as nose drops and any other suitable known vaccination routes.

Chickens vaccinated with live vaccine containing the MB and/or MB-2 and/or MB-1 viruses respond with precipitating and type specific neutralizing antibodies and they were immune to subsequent infection with an Israeli virulent IBD virus strain, as well as infection with a European strain. Thus, vaccines according to the invention appear to confer universal immunity against IBD.

The above discussion provides a factual basis for the use of novel virus strains as a vaccine against infectious bursal disease in poultry. The methods used with, and the utility of, the present invention can be shown by the following examples.

EXAMPLES

Example 1

Attenuation of the Strains

The original viruses were isolated from bursae of Fabricius of broiler chickens that died of IBD on two farms in the central part of Israel during the year of 1989. The bursae were ground, centrifuged and filtered through 0.2 $\mu$ Millipore filter. The filtrates were injected into the allantoic cavity of 11-days-embryonated SPF chicken eggs. After incubation for 72–96 hours the embryos and membranes were collected, homogenized and reinjected serially to SPF chicken embryonated eggs for attenuation.

Strain MB (ECACC No. V92052301) was passaged 43 times, strain MB-1 (ECACC No. V92102209) was passaged 94 times and strain MB-2 (ECACC No. V92100106), isolated from another farm, was passaged 71 times. These passaged strains were lyophilized and served as working seeds.

Example 2

Vaccination of Maternally Immune (M.I.) Broiler Chicks with MB Vaccine

Broiler chicks (15 per group) were vaccinated at different ages: A single vaccination at 2, 7 or 14 days, or two vaccinations at 2 and 14 days (Table 1). The chicks were in isolation units throughout the entire experiment. Vaccination was via drinking water system with $10^{3.35}$ $EID_{50}$ MB virus per dose. Maternal antibodies at 2, 7 and 14 days post hatch were 11/11, 6/10 and 2/10 respectively (No. of AGP positive/No. of sera tested; AGP=Agar Gel Precipitin). Efficacy was evaluated at 28 days by two methods:

(a) Serological response: precipitating antobodies (AGP) or Enzyme Linked Immunosorbent Assay (ELISA). A very good correlation was found between these systems.

(b) Protection against challenge: Birds were challenged at 28 days of age with an Israeli virulent IBD virus strain—$10^5$ $EID_{50}$ per chick intraocularly. Challenge with the Weybridge challenge 52/70 strain was also performed. Three days later birds were sacrificed and their bursae of Fabricius tested for presence of IBD virus by AGP. Immunized birds would be negative while susceptible ones would be positive. Identical results were obtained for challenges with the virulent Israeli strain of IBD virus and the Weybridge 52/70 strain. Thus, the vaccines according to the invention confer immunity against both Israeli and European strains.

The bursa/body weight ratio was calculated and bursae were tested for histopathological lesions. All groups were also vaccinated with a live commercial lentogenic Newcastle Disease (NDV) Vaccine at 14 days of age.

TABLE 1

| Age of Vaccination (days) | Serological Response to IBD | | Birds Protected Against Challenge | Antibodies to NDV (HI) | Body Weight (gm) |
|---|---|---|---|---|---|
| | AGP | ELISA | | | |
| 2 | 0/14* | 1/14 | 2/12** | 3.6 ± 0.9 | 1077 ± 92 |
| 2 + 14 | 13/14 | 13/14 | 14/14 | 3.1 ± 0.5 | 1077 ± 148 |
| 7 | 6/14 | 7/14 | 14/14 | 3.5 ± 0.9 | 958 ± 119 |
| 14 | 15/15 | 15/15 | 14/14 | 3.8 ± 0.8 | 1114 ± 83 |
| control | 0/8 | 0/8 | 0/8 | 3.8 ± 0.9 | 995 ± 88 |

*No. positive/No. tested
**No. protected/No. tested

From the results shown in Table 1 it can be seen that chicks are protected when vaccinated with MB strain vaccine at 7 days of age or older.

At 7 days about half of the birds responded serologically and all of them were protected against challenge. At 14 days all of the birds were immune, as seen serologically and by resistance to challenge. No protection was observed when vaccination took place at 2 days of age. The bursa/body weight ratio 3 days after exposure to virulent virus was close to 0.25% in the unprotected groups (controls and vaccinated at 2 days) and was 0.07% in the protected groups (2+14, 7 and 14 days). This figure indicates that the virus broke through maternal antibodies and caused atrophy of the bursa. Histopathological examination revealed mild lymphocyte depletion. The response to NDV vaccination in the IBD vaccinated groups was similar to that of the control group. Body weight of IBD vaccinated birds at the end of the experiment was not statistically different from that of the control group.

Example 3
Oral or Aerosol Vaccination of M.I. Broiler Chicks with MB and MB-1 Vaccine Broiler chicks housed in isolators from day 1 were vaccinated at either 12 days of age (groups 1 and 2, MB or MB-1 vaccine) or at 1+12 days (groups 3 and 5, MB vaccine) with a dose of $10^{3.65}$ $EID_{50}$. Birds were vaccinated with live NDV vaccine (VH strain) at 1+18 days of age via ocular route (groups 1–4) or at 1+12 days of age via aerosol route (groups 5–6). In group 5 a combined aerosol vaccination of IBDV (MB) and NDV (VH) was performed. The chicks were bled and challenged at 29 days of age and sacrificed 3 days later. At day 1, 10/10 of chicks had IBD maternally derived antibodies.

MB and MB-1 vaccines conferred excellent protection against challenge and moderate serological response when administered by drinking water or by aerosol. It seems from this and from the previous example that one vaccination at 12–14 days of age immunizes as well as two vaccinations at 1 and at 12–14 days.

No adverse effect on body weight or NDV titer could be observed, even though some degree of bursa atrophy was observed.

It can further be concluded that simultaneous vaccination with MB strain of Gumboro and with New Castle disease vaccine is possible, leading to similar results compared to separate

TABLE 2

| IBD Vaccination | | | | Serological Response | | Birds Protected Against Challenge | Antibodies to NDV (HI) | Body Weight (gm) |
|---|---|---|---|---|---|---|---|---|
| Group | Days | Method | Strain | AGP | ELISA | | | |
| 1 | 12 | dw* | MB-1 | 7/8 | 7/8 | 8/8 | 4.0 ± 0.8 | 1304 ± 109 |
| 2 | 12 | dw | MB | 7/8 | 8/8 | 8/8 | 4.6 ± 1.0 | 1348 ± 131 |
| 3 | 1 + 12 | dw | MB | 10/16 | 9/16 | 16/16 | 4.3 ± 0.7 | 1209 ± 116 |
| 4 | control | — | — | 0/8 | 0/8 | 0/8 | 4.2 ± 0.9 | 1256 ± 163 |
| 5 | 1 + 12 | aerosol** | MB | 10/16 | 10/16 | 16/16 | 4.0 ± 0.9 | 1031 ± 99 |
| 6 | control | — | — | 0/14 | 0/14 | 0/14 | 4.7 ± 0.7 | 1154 ± 102 | dw* = drinking water
**Combined IBDV + NDV vaccination vaccinations. This combined vaccination was via the respiratory system using aerosol technique which is recommended for NDV vaccination. It is further demonstrated that aerosol vaccination is a good way for mass vaccination with MB vaccine.

Example 4
Comparison of MB Strain with Attenuated Winterfield Strain 14 days old broiler chicks were vaccinated via ocular route with MB strain ($10^{3.75}$ $EID_{50}$ per bird) or with Winterfield strain ($10^{4.28}$ $EID_{50}$ per bird). The Winterfield strain is an attenuated strain that does not protect flocks against current more pathogenic viruses. Two control groups were not vaccinated with IBDV. Three groups were vaccinated with NDV vaccine at day 1 and day 17. At 31 days of age all birds were bled and challenged. Results are summarized in Table 3.

TABLE 3

| Vaccination | | Antibodies against | | Protection |
|---|---|---|---|---|
| IBDV | NDV | IBDV | NDV | against challenge |
| MB | VH | 10/10 | 5.2 | 10/10 |
| Winterfield | VH | 0/10 | 5.1 | 0/10 |

TABLE 3-continued

| Vaccination | | Antibodies against | | Protection |
|---|---|---|---|---|
| IBDV | NDV | IBDV | NDV | against challenge |
| — | VH | 0/18 | 4.7 | 0/18 |
| — | — | 0/20 | 2.3 | 0/20 |

It can be seen from Table 3 that: (a) Winterfield strain does not protect against challenge, nor did it produce anti-IBD antibodies; (b) MB strain confers high protection and high antibodies level; and (c) MB strain had no adverse effect on NDV antibodies titer.

Example 5
Vaccination of Chicks with MB or MB-2 Vaccines Using Different Doses

Vaccination took place in isolation units (one unit per experimental group) via eye-drop at 7 or 12 days of age. Different doses in the range of $10^{1.0}$ to $10^{3.35}$ $EID_{50}$ were tested. In this example commercial M.I. broiler chicks as well as SPF chicks were vaccinated and the results are summarized in Table 4 and Table 5, respectively. At 21 days of age (9 or 14 days post-vaccination) birds were bled and challenged. Four days later they were sacrificed, their bursae tested for IBD antigen and the bursa/body weight ratio was calculated.

TABLE 4

M.I. Broiler Chicks

| Vaccine | Age of Vacc. days | Dose $EID_{50}$ | Serological Resp. | Protec. Against Challenge | Bursa to Body | |
|---|---|---|---|---|---|---|
| | | | | | Body Ratio-% | Weight (gr) |
| MB | 7 | $10^{3.35}$ | 14/17 | 17/17 | 0.07 ± 0.03 | 900 ± 69 |
| MB | 12 | $10^{2.35}$ | 9/10 | 10/10 | 0.07 ± 0.02 | 921 ± 95 |
| MB | 12 | $10^{1.35}$ | 9/11 | 11/11 | 0.07 ± 0.01 | 918 ± 86 |
| Control | — | | 0/11 | 0/11 | 0.29 ± 0.06 | 915 ± 72 |
| MB-2 | 12 | $10^{3.0}$ | 5/10 | 10/10 | 0.07 ± 0.03 | 988 ± 88 |
| MB-2 | 12 | $10^{2.0}$ | 5/10 | 10/10 | 0.07 ± 0.02 | 974 ± 94 |
| MB-2 | 12 | $10^{1.0}$ | 4/10 | 10/10 | 0.10 ± 0.03 | 988 ± 93 |

TABLE 5

SPF Chicks

| Vaccine | Age of Vacc. (days) | Dose $EID^{50}$ | Mort. Post Vaccntn. | Serological Resp. | Protec. Against Challenge | Bursa to Body | |
|---|---|---|---|---|---|---|---|
| | | | | | | Body Ratio-% | Weight (gr) |
| MB | 7 | $10^{3.35}$ | 5/18 | 7/7 | 7/7 | 0.12 ± 0.03 | 277 ± 40 |
| MB | 12 | $10^{2.35}$ | 4/15 | 5/6 | 6/6 | 0.11 ± 0.03 | 199 ± 20 |
| MB | 12 | $10^{1.35}$ | 4/15 | 5/6 | 6/6 | 0.14 ± 0.02 | 212 ± 33 |
| Control | — | | 0/15 | 0/3* | 0/8* | 0.43 ± 0.17 | 205 ± 13 |
| MB2 | 12 | $10^{3.0}$ | 0/15 | 5/8 | 8/8 | 0.11 ± 0.02 | 264 ± 27 |
| MB2 | 12 | $10^{2.0}$ | 0/15 | 7/8 | 8/8 | 0.13 ± 0.03 | 224 ± 44 |
| MB2 | 12 | $10^{1.0}$ | 0/15 | 6/8 | 8/8 | 0.12 ± 0.02 | 233 ± 17 |

*5 chicken out of 8 died as a result of the challenge. Antigen found in 3 survivors. No death occurred after the challenge in any of the vaccinated groups.

It can be seen (Tables 4, 5) that MB and MB-2 vaccines conferred excellent protection against challenge as early as 9 days post-vaccination and good serological response, even at a dose as low as $10^1$ $EID_{50}$.

MB-2 is less pathogenic than MB (see mortality post-vaccination in SPF chicks Table 5) and it evokes a somewhat weaker serological response.

Example 6
Vaccination of SPF-1 Day Old Chicks With MB, MB-1 and MB-2 Strains

SPF chicks at 1 day of age were vaccinated in isolation units via eye drops, $10^{3.35}$ $EID_{50}$ per dose. At 7 days post vaccination part of each group was sacrificed and bursa/body weight ratio was calculated. At 21 days of age the remaining chicks were challenged and the procedure was similar to that described in Example 5.

TABLE 6

| Vaccine | 7 dpi* Bursa/body ratio % | Mortality after vaccination | Serological Response IBD | Protection against Challenge |
|---|---|---|---|---|
| MB | 0.12 ± 0.03 | 8/18 | 2/6 | 6/6 |
| MB-1 | 0.15 ± 0.04 | 3/18 | 0/7 | 7/7 |
| MB-2 | 0.12 ± 0.03 | 0/18 | 2/9 | 9/9 |
| Control | 0.29 ± 0.05 | 0/15 | 0/8 | 0/8 |

*dpi = days post-immunization.

It can be seen from Table 6 that the degree of pathogenicity to 1 day old SPF chicks (measured by mortality rate) is higher for MB, lower for MB-1 and zero for MB-2. Protection against challenge is very good for all strains.

Example 7
Identification of MB and MB-2 Viral Proteins
A. Preparation of Viral Proteins for Analysis Chicks were reared in isolation up to 4 weeks of age, divided into groups and infected as follows:

Group 1 was infected with a wild type pathogenic virus isolated in Israel.

Group 2 was infected with another isolate of IBDV from which the MB strain of the invention was developed by egg passages.

Group 3 was infected with the MB strain (Deposit No. V92100106).

Group 4 was infected with a further isolate of IBDV from which with MB-2 (Deposit No. V92100106) was developed by egg passages.

Group 5 was infected with the MB-2 strain (Deposit No. V92100106).

Three days post-infection the chickens were sacrificed and their bursae of Fabricius were homogenized, frozen and thawed. Viral particles of each group were banded between 40% to 60% sucrose in an ultracentrifuge.

B. Western Blot Analysis

Figure 1B:
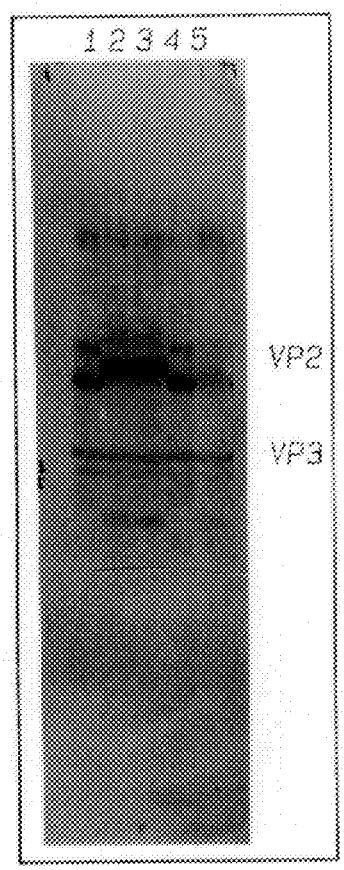

Following SDS treatment the proteins were separated on SDS-PAGE (Sodium Dodecyl Sulfate—Polyacryl Amide Gel Electrophoresis) for 14 hours at 9 W. Half of each gel was stained with coomasie blue and half was transferred to hybond-C filters for reaction with SPF negative serum (Gel A) or with convalescent chicken serum (Gel B). The gels were reacted with rabbit anti-chicken serum and peroxidase. FIG. 1 is a representative example of such an experiment. Lanes 1–5 in each gel correpsond to Groups 1–5 detailed above. vp=viral protein.

It can be seen from Picture 1 that convalescent serum (Gel B) reacted with VP2 and VP3 of IBD virus whereas SPF negative serum did not react with these viral proteins (Gel A).

Furthermore, it can be seen that:

a) VP2 of MB and its originator strain—Lanes 2 and 3—differ by size from the wild type strain (Lane 1).

b) VP2 of the attenuated MB-2 strain (Lane 5) reacted with the convalescent serum less intensively than VP2 of its originator strain (Lane 4).

Its position on the gel is similar to VP2 of all other viruses except that of MB and MB originator.

It was of great importance to find out that MB-2 differs clearly from its' originator strain and that MB differs from most other IBD viruses isolated in Israel.

Example 8

Lack of Reversion to Virulence

The aim of this example is to show that the degree of resiual pathogenicity of the MB strain does not change during passages of the virus from bird to bird. 15 SPF chicks were vaccinated at 1 day of age with MB virus ($10^{3.65}$ $EID_{50}$ per chick). Three days later five chicks were sacrificed and their bursa served for infection of a second group of 1 day old chicks. Seven days after each infection the virulence of the virus was measured by:

a) Bursa/body weight ratio; and b) Histopathological examination of the bursa.

Five such successive bird-to-bird passages were performed. With each passage a control group was infected with MB strain and a comparison was made between pathogenicity of the bird-passaged virus and the pathogenicity of the MB infection inoculates. Pathogenicity of first MB infection, as expressed by two indices, i.e., Bursa/Body weight ratio and histopathological score, was arbitrarily defined 1.00 and is termed "pathogenicity index" in Table 7.

TABLE 7

|  | Pathogenicity Index[a] | | |
| --- | --- | --- | --- |
|  | IBDV titer $EID_{50}$/dose | Bursa/body weight ratio[b] | Histopathology[c] |
| 1st MB infection | $10^{3.65}$ | 1.00 | 1.00 |
| 1st bird passage | $>10^{6.3}$ | 0.93 | 0.88 |
| 2nd bird passage | $10^{5.62}$ | 0.92 | 0.96 |
| 3rd bird passage | $10^{4.92}$ | 1.00 | 0.96 |
| 4th bird passage | $10^{4.93}$ | 1.07 | 1.04 |
| 5th bird passage | $10^{4.65}$ | 0.93 | 1.04 |

[a]Pathogenicity index: pathogenicity of bird passaged virus relative to pathogenicity of 1st MB infection (defined as 1.00).
[b]Bursa/body weight ratio of 1st MB infected chicks was from 0.12% to 0.15% while bursa/body weight ratio of uninfected 7 days old chicks was 0.30%.

TABLE 7-continued

|  | Pathogenicity Index[a] | |
| --- | --- | --- |
| IBDV titer $EID_{50}$/dose | Bursa/body weight ratio[b] | Histopathology[c] |

[c]Histopathological score: 0-normal, no lymphoid depletion; 4-severe lymphoid depletion. The hispathological score of first MB infection was from 2.5 to 2.9, while the hispathological score of the uninfected control was 0.23.

It can be concluded from Table 7 that the pathogenicity of MB strain was not elevated during five bird-to-bird passages.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

What is claimed is:

1. A lyophilized virus composition containing an attenuated strain of the Infectious Bursal Disease virus deposited at the ECACC under NO. V92052301 (MB).

2. A lyophilized virus composition containing an attenuated strain of the Infectious Bursal Disease virus deposited at the ECACC under NO. V92100106 (MB-2).

3. A lyophilized virus composition containing an attenuated strain of the Infectious Bursal Disease virus deposited at the ECACC under NO. V92102209 (MB-1).

4. A vaccine for the prevention of Infectious Bursal Disease in poultry comprising an effective immunizing amount of a live attenuated intermediately pathogenic Infectious Bursal Disease virus belonging to the strain deposited at the ECACC under No. V92052301 (MB).

5. A vaccine for the prevention of Infectious Bursal Disease in poultry comprising an effective immunizing amount of a live attenuated intermediately pathogenic Infectious Bursal Disease virus belonging to the strain deposited at the ECACC under No. V92100106 (MB-2).

6. A vaccine for the prevention of Infectious Bursal Disease in poultry comprising an effective immunizing amount of a live attenuated intermediately pathogenic Infectious Bursal Disease virus belonging to the strain deposited at the ECACC under No. V92102209 (MB-1).

7. A vaccine for the prevention of Infectious Bursal Disease in poultry comprising an effective immunizing amount of at least one live attenuated Infectious Bursal Disease virus selected from the group consisting of the strains deposited at the ECACC under Nos. V92052301 (MB), V92100106 (MB-2) and V92102209 (MB-1).

8. A vaccine for poultry comprising:

a) an effective immunizing amount of at least one live attenuated Infectious Bursal Disease virus selected from the group consisting of the strains deposited at the ECACC under Nos. V92052031 (MB), V92100106 (MB-2), and V92102209 (MB-1); and b) an effective immunizing amount of at least one additional poultry disease virus other than Infectious Bursal Disease Virus (IBDV).

9. A vaccine for poultry according to claim 8 wherein said additional poultry disease virus is selected from the group consisting of Lentogenic New Castle Disease virus, Marek Disease virus, and Infectious Bronchitis virus.

10. A method of protecting poultry against Infectious Bursal Disease which comprises administering to the birds an effective immunizing amount of a vaccine selected from the group consisting of a vaccine according to claim 7 and a vaccine according to claim 7 with at least one additional poultry disease virus other than Infectious Bursal Disease Virus (IBDV).

11. A method according to claim 10 wherein said effective immunizing amount is from about $10^1$ to $10^4$ $EID_{50}$ per dose.

12. A method of protecting poultry and, which comprises administering to the chickens an effective immunizing amount of a vaccine according claim 9.

13. A method according to claim 10 which comprises a single administration at any age of vaccination.

14. A method according to claim 10 which comprises repeated administrations of the vaccine.

15. A method according to claim 10 or 12 wherein said vaccine is administered via drinking water.

16. A method according to claim 10 or 12 wherein said vaccine is administered as eyedrops via the ocular route.

17. A method according to claim 10 or 12 wherein said vaccine is administered as nose drops via the nasal route.

18. A method according to claim 10 or 12 wherein said vaccine is administered by spraying the birds with said vaccine.

19. A method for the preparation of a live vaccine which protects poultry against Infectious Bursal Disease comprising the steps of:

(a) growing an Infectious Bursal Disease virus in a medium selected from the group consisting of specific pathogenic free (SPF) embryonated chicken eggs, chicken embryo fibroblasts (CEF) and Vero cell line;

(b) harvesting the virus material obtained under step (a);

(c) stabilizing the material obtained in step (b); and (d) lyophilizing the material obtained in step (c);

wherein the Infectious Bursal Disease virus grown in step (a) is a virus of one of the strains selected from the group consisting of MB (ECACC Deposit No. V92052301), MB-1 (EACC Deposit No. 92102209) and MB-2 ECACC Deposit No. 92100106).

* * * * *